US00PP35697P2

(12) United States Plant Patent
Clark

(10) Patent No.: US PP35,697 P2
(45) Date of Patent: Mar. 12, 2024

(54) ***COLEUS* PLANT NAMED 'UF22-129-3'**

(50) Latin Name: *Coleus scutellarioides*
Varietal Denomination: UF22-129-3

(71) Applicant: Florida Foundation Seed Producers, Inc., Marianna, FL (US)

(72) Inventor: David G. Clark, Gainesville, FL (US)

(73) Assignee: Florida Foundation Seed Producers, Inc., Marianna, FL (US)

( * ) Notice: Subject to any disclaimer, the term of this patent is extended or adjusted under 35 U.S.C. 154(b) by 0 days.

(21) Appl. No.: 18/445,284

(22) Filed: Jun. 20, 2023

(51) Int. Cl.
*A01H 6/00* (2018.01)
*A01H 5/12* (2018.01)

(52) U.S. Cl.
USPC ..... Plt./469

(58) Field of Classification Search
USPC ..... Plt./469
CPC ..... A01H 6/00; A01H 5/12
See application file for complete search history.

(56) References Cited

U.S. PATENT DOCUMENTS

PP25,651 P3 6/2015 Clark et al.

*Primary Examiner* — Keith O. Robinson
(74) *Attorney, Agent, or Firm* — Koenig IP Works, PLLC; Katherine Koenig

(57) ABSTRACT

'UF22-129-3' is a new *Coleus* plant, selected for having a combination of novel vigorous upright growth habit, and highly lobed and ruffled leaves that are colored bright yellow green with distinct pale yellow green and greenish yellow midveins and accents. 'UF22-129-3' maintains these contrasting colors and patterns in both sun and shade. 'UF22-129-3' is extremely vigorous and fast-growing with excellent lateral branching. 'UF22-129-3' is upright in habit, but it is highly branched and spreading in form, growing wider than it does tall.

3 Drawing Sheets

Genus and species: *Coleus scutellarioides*.
Cultivar denomination: 'UF22-129-3'.

CROSS-REFERENCE TO RELATED APPLICATIONS

N/A.

ACKNOWLEDGEMENT OF FEDERAL RESEARCH SUPPORT

N/A.

BACKGROUND OF THE NEW CULTIVAR

The invention relates to a new and distinct cultivar of *Coleus* plant named 'UF22-129-3'. The new cultivar 'UF22-129-3' originated from an open pollination conducted in May-November 2019 in Citra, Florida, between the female *Coleus* plant 'UF21-58-7' (unpatented) and an unknown male *Coleus* plant. A single seedling was chosen in May 2020 for further asexual propagation in Gainesville, Florida.

The new cultivar 'UF22-129-3' has been reproduced asexually for over 18 months through vegetative meristem tip cuttings and has been found to retain its distinctive characteristics through successive asexual propagations. 'UF22-129-3' was first propagated asexually by vegetative meristem tip cuttings in May 2020 in Gainesville, Florida, and has remained true-to-type since that time.

Plant Breeder's Rights for the new cultivar 'UF22-129-3' have not been applied for, and 'UF22-129-3' has not been made publicly available more than one year prior to the filing date of this application.

SUMMARY OF THE INVENTION

The new cultivar 'UF22-129-3' has not been observed under all possible environmental conditions. The phenotype of the new cultivar may vary with variations in environment and cultural practices such as temperature, light intensity, fertilization, irrigation, and application of plant growth regulators without any change in genotype.

The new cultivar 'UF22-129-3' was selected for its consistent foliage color patterning, and also for its fast growth rate and vigor in the greenhouse and landscape. 'UF22-129-3' has foliage that is predominantly colored bright yellow green with midveins and accents colored pale yellow green and greenish yellow. Normally this color combination changes in either full sun (predominantly brighter green with more contrast) or full shade (predominantly darker green with less contrast). However, 'UF22-129-3' is exceptional because it maintains consistent contrasting colors in both sun and shade.

The following are the most outstanding and distinguishing characteristics of 'UF22-129-3' when grown under normal horticultural practices in Gainesville, Florida: (1) 'UF22-129-3' has the combination of vigorous, upright habit and spreading growth form, excellent heat tolerance, and consistent multi-colored leaves that are significantly different than other *Coleus* plants; (2) it has superior stability in foliage color in both sun and shade conditions, and it has a vigorous growth habit with excellent lateral branching, making it suitable for propagators and producers; and (3)

'UF22-129-3' has been observed to have long-season performance in landscape trials in Gainesville, Florida.

When compared to the female parent 'UF21-58-7', 'UF22-129-3' has large, highly lobed and ruffled leaves that are as long as they are wide, whereas 'UF21-58-7' has large, highly lobed leaves that are longer than they are wide. Additionally, 'UF22-129-3' has leaves that are predominantly colored yellow green with pale yellow green midveins and accents across the leaf, whereas 'UF21-58-7' has leaves that are colored primarily pink with maroon accents and chartreuse margins. Further, 'UF'22-129-3' has a vigorous, upright habit with a spreading form that is well-branched, whereas 'UF21-58-7' is less vigorous, with a more compact habit and less horizontal spread.

DESCRIPTION OF THE FIGURES

This new *Coleus* cultivar 'UF22-129-3' is illustrated by the accompanying photographs, which show the plant's form and foliage. The colors shown are as true as can be reasonably obtained by conventional photographic procedures.

FIG. 2 shows the growth habit, form, and foliage of the new *Coleus* cultivar; and FIG. 3 shows a close-up view of the foliage of the new *Coleus* cultivar.

DETAILED BOTANICAL DESCRIPTION OF THE CULTIVAR

Figure 1:
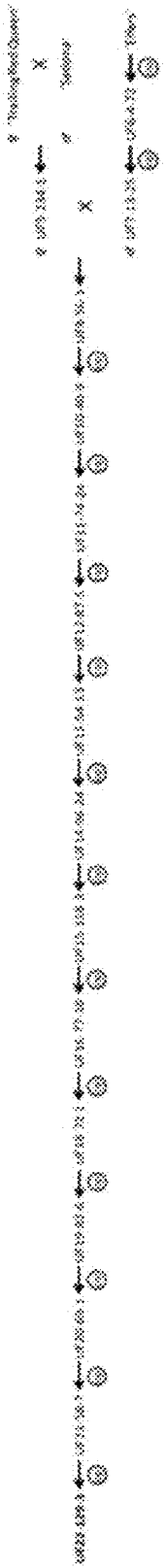
FIG. 1 shows the pedigree of the new *Coleus* cultivar 'UF22-129-3' as is shown and described herein.
Figure 2:
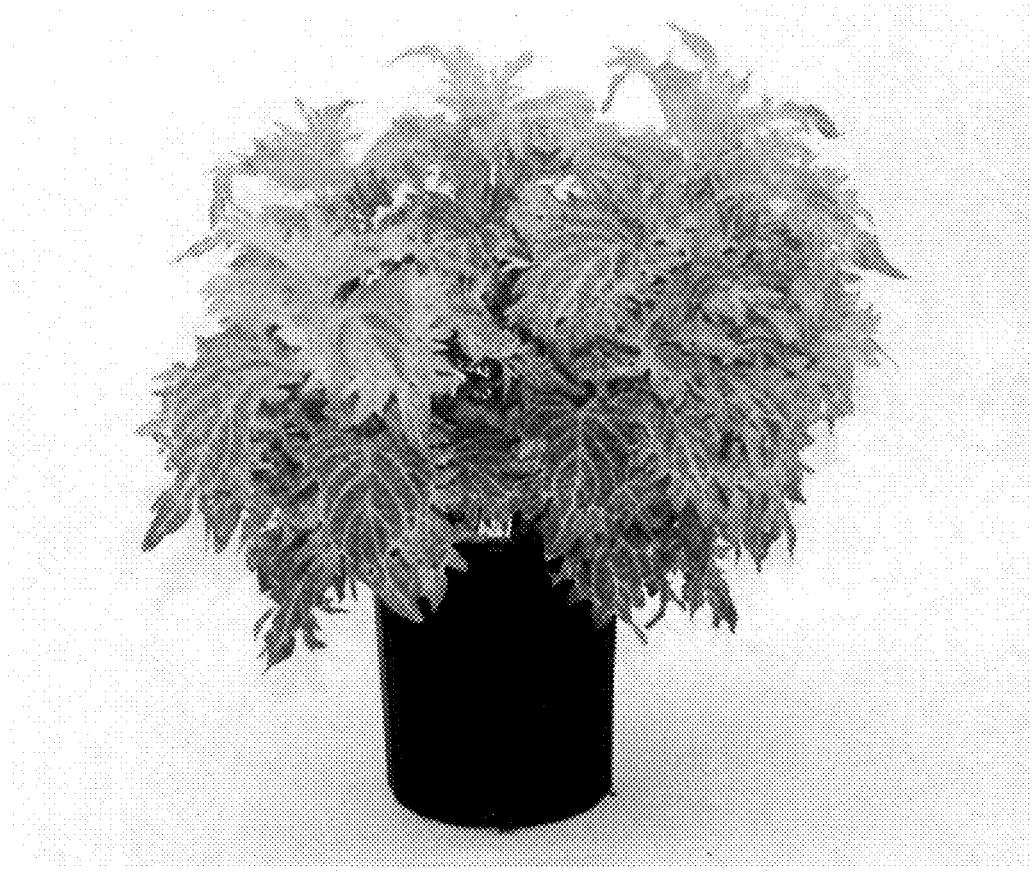
FIGS. 2 and 3 were taken from plants grown eleven weeks from unrooted cuttings in September-December 2022 in a glass-covered greenhouse in Gainesville, Florida.
Figure 3:
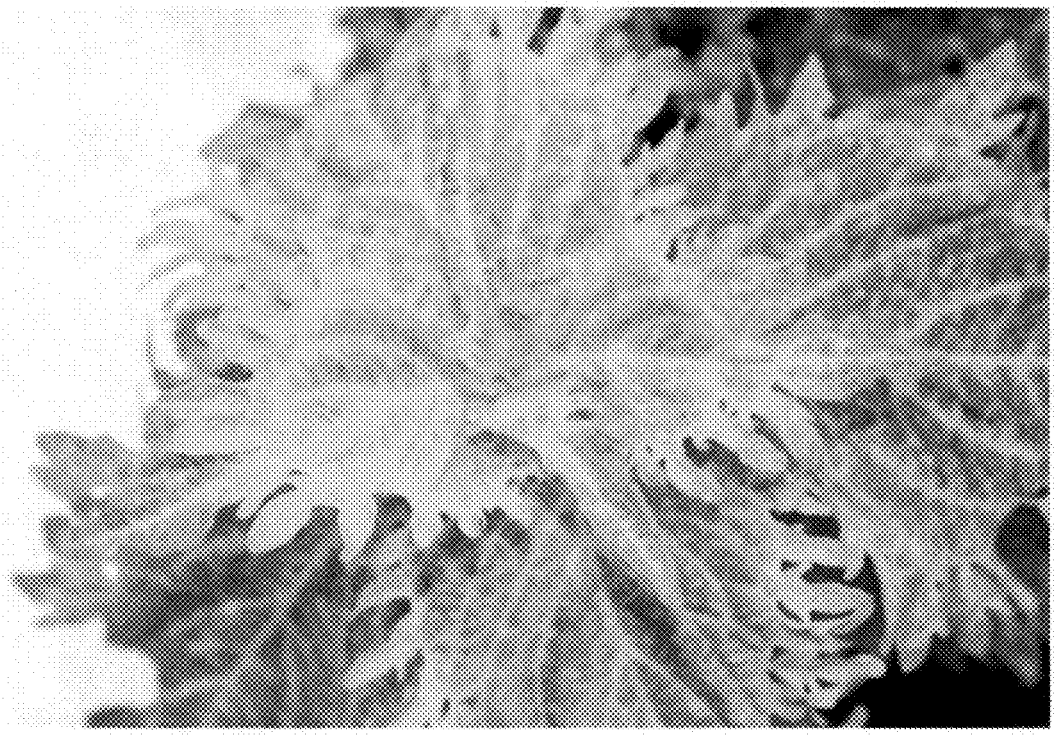

Foliage color was determined under full sun conditions in the middle of the day in a glass-covered greenhouse. Color references are to The R.H.S. Colour Chart of The Royal Horticultural Society of London (R.H.S.), 2007 5th Edition. *Coleus* leaves are rarely one solid color but encompass hues, shades and tints, and color patterns differ from one genotype to another due to varying levels of variegation. The following detailed description of 'UF22-129-3' was obtained using eleven-week-old plants grown from unrooted cuttings in September-December 2022 in a glass-covered greenhouse in Gainesville, Florida. The plants were propagated in mist for ten days after cuttings were stuck, pinched, then grown in one-gallon pots for approximately nine and a half additional weeks.

BOTANICAL DESCRIPTION

Botanical classification:
- Family.—Lamiaceae.
- *Botanical name.—Coleus scutellarioides.*
- *Common name.—Coleus.*
- *Cultivar name.*—'UF22-129-3'.

Parentage:
- *Female or seed parent.*—'UF21-58-7'.
- *Male or pollen parent.*—Unknown.

Plant description:
- *Form.*—Spreading.
- *Habit.*—Upright.
- *Height* (*from top of soil*).—25-30 cm.
- *Width* (*horizontal plant diameter*).—50-55 cm.

Propagation:
- *Type cuttings.*—Vegetative meristems having at least 1 node.
- *Time to initiate roots.*—3-4 days.
- *Time to produce a rooted cutting.*—7-10 days.
- *Root habit.*—Fibrous.
- *Root description.*—Callus forms in 2-3 days, roots initiate in 3-4 days and become a highly branched cutting in 7-10 days.

Branches:
- *Quantity per plant.*—Approximately 6-7.
- *Branch color.*—RHS 143C (yellow green).
- *Texture.*—Smooth.
- *Pubescence.*—Not present.
- *Stem description.*—Square-shaped stem.
- *Branch diameter.*—0.8-0.9 cm at the base of a 25-cm-long branch.
- *Branch length.*—20-25 cm.
- *Internode length.*—3.5 cm measured at mid-branch.
- *Anthocyanin.*—Not present.

Leaves:
- *Quantity of leaves per branch.*—Approximately 20-22.
- *Arrangement.*—Opposite.
- *Fragrance.*—Not fragrant.
- *Shape.*—Ovate.
- *Length.*—12-13 cm.
- *Width.*—11-12 cm.
- *Apex.*—Broadly acute.
- *Base.*—Attenuate.
- *Margin.*—Highly lobed.
- *Leaf texture.*—Adaxial (top): Pulverulent. Abaxial (bottom): Smooth.
- *Venation color* (*both upper and lower surfaces*).—RHS 157B (pale yellow green) and greenish yellow (RHS 1B).
- *Venation pattern* (*both upper and lower surfaces*).—Reticulate.
- *Color, immature leaf.*—Upper surface: Major color: RHS 140A (yellowish green). Veins and accents: RHS 1B (greenish yellow). Lower surface: RHS 143C (yellow green).
- *Color, mature leaf.*—Upper surface: Major color: RHS 140A (yellow green). Veins and accents: RHS 157B (pale yellow green) and RHS 1B (greenish yellow). Lower surface: RHS 141C (yellowish green).
- *Petiole length.*—3 cm.
- *Petiole diameter.*—0.3-0.4 cm.
- *Petiole color.*—RHS 145B.
- *Petiole texture.*—Smooth, no pubescence.

Flowers and seeds: Flowers and seeds have not been observed during formal trials in Gainesville, Florida.

Fruit/seed set: Fruit/seed not observed.

Disease and insect resistance: Disease and insect resistance is typical of the species, thus no claims are made of any superior disease or insect resistance with this cultivar. The most common insect pests observed on this plant in Gainesville, Florida have been long-tailed or citrus mealybugs (*Pseudococcus* spp.), which occur on older stock plant material held in the greenhouse for over 3-4 months. Impatiens Necrotic Spot Virus (*Bunyaviridae*) has also been observed in plants confined in greenhouses with mixed crops (peppers) infected with Western flower thrips (*Frankliniella occidentalis*). The most common pathogen of this species in the U.S. is downy mildew (*Perononspora lamii*). This pathogen has been observed in stock materials grown closely together in cooler growing seasons.

COMPARISON WITH KNOWN CULTIVARS

When compared to the *Coleus* cultivar 'UF12-62-2' (U.S. Plant Pat. No. 25,651, commercial name Mainstreet River Walk), the new *Coleus* cultivar 'UF22-129-3' has a predominant leaf coloration of bright yellowish green with veins and accents colored in a mixture of pale yellow green and greenish yellow on the upper surface of mature leaves, whereas 'UF12-62-2' has a prominent leaf coloration of a strong yellow green with veins and accents colored pale yellow on the upper surface of mature leaves. Additionally, UF22-129-3 has leaf margins that are deeply lobed , whereas 'UF12-62-2' has leaf margins that are less lobed and more crenate in shape.

What is claimed is:

1. A new and distinct *Coleus scutellarioides* plant named 'UF22-129-3' as shown and described herein.

* * * * *